United States Patent
Hummelshøj

(10) Patent No.: US 10,596,012 B2
(45) Date of Patent: Mar. 24, 2020

(54) ARTIFICIAL LIMB FOR HOST ASSISTANCE

(71) Applicant: Toyota Research Institute, Inc., Los Altos, CA (US)

(72) Inventor: Jens Strabo Hummelshøj, Burlingame, CA (US)

(73) Assignee: Toyota Research Institute, Inc., Los Altos, CA (US)

(*) Notice: Subject to any disclaimer, the term of this patent is extended or adjusted under 35 U.S.C. 154(b) by 112 days.

(21) Appl. No.: 15/796,175

(22) Filed: Oct. 27, 2017

(65) Prior Publication Data

US 2019/0125551 A1 May 2, 2019

(51) Int. Cl.
*A61F 2/60* (2006.01)
*A61F 2/76* (2006.01)
(Continued)

(52) U.S. Cl.
CPC ............... *A61F 2/604* (2013.01); *A61F 2/50* (2013.01); *A61F 2/54* (2013.01); *A61F 2/60* (2013.01); *A61F 2/70* (2013.01); *A61F 2/76* (2013.01); *A61F 5/01* (2013.01); *A61F 2/588* (2013.01); *A61F 2/601* (2013.01); *A61F 2/78* (2013.01); *A61F 2002/6614* (2013.01); *A61F 2002/701* (2013.01); *A61F 2002/704* (2013.01); *A61F 2002/745* (2013.01);
(Continued)

(58) Field of Classification Search
CPC ...... A61F 2/64; A61F 2/76; A61F 2/60; A61F 2/604; A61F 2/80; A61H 3/0244; A61H 3/008; F16M 13/04; B25J 9/0006; G05B 2219/40305
See application file for complete search history.

(56) References Cited

U.S. PATENT DOCUMENTS 406,328 A * 7/1889 Yagn ...................... A63B 25/10
482/77
3,265,429 A * 8/1966 Shatt ......................... B25J 1/04
294/104

(Continued)

OTHER PUBLICATIONS

Festo. Festo use biometry to create a fish tail and robotic elephant trunk. Apr. 9, 2016. Date verified by the Wayback Machine. (Year: 2016).*

(Continued)

*Primary Examiner* — Christie L Bahena
(74) *Attorney, Agent, or Firm* — Christopher G. Darrow; Darrow Mustafa PC

(57) ABSTRACT

System, methods, and other embodiments described herein relate to a device for providing mobility assistance to a user. In one embodiment, a mobility system includes a support component including at least a waist device that is configured to secure the mobility system to the user at a waist area of the user. The mobility system includes a limb attached to the support component and extendable from the support component to a floor when the user is in a standing position. The limb is configured to support the user by providing a rigid structure between the floor and the user. The limb is configured to assist the user in transitioning from a seated position to the standing position by applying a substantially upward force to the user through the support component when transitioning to the standing position.

14 Claims, 10 Drawing Sheets

(51) Int. Cl.
*A61F 2/50* (2006.01)
*A61F 2/54* (2006.01)
*A61F 2/70* (2006.01)
*A61F 5/01* (2006.01)
*A61F 2/78* (2006.01)
*A61H 3/00* (2006.01)
*A61F 2/68* (2006.01)
*A61F 2/74* (2006.01)
*A61F 2/66* (2006.01)
*A61F 2/58* (2006.01)

(52) U.S. Cl.
CPC ............... *A61F 2002/7615* (2013.01); *A61F 2002/7862* (2013.01); *A61H 3/008* (2013.01); *A61H 2003/001* (2013.01); *A61H 2003/002* (2013.01); *A61H 2003/007* (2013.01)

(56) References Cited

U.S. PATENT DOCUMENTS

| | | | |
|---|---|---|---|
| 6,104,379 A * | 8/2000 | Petrich | G06F 3/014 345/156 |
| 9,138,369 B1 | 9/2015 | Chadwell | |
| 9,526,635 B2 | 12/2016 | Gilbert et al. | |
| 9,586,129 B2 | 3/2017 | Henrie et al. | |
| 2003/0223844 A1* | 12/2003 | Schiele | A61H 1/0274 414/5 |
| 2007/0056592 A1 | 3/2007 | Angold et al. | |
| 2007/0123997 A1* | 5/2007 | Herr | A61F 2/60 623/27 |
| 2010/0256537 A1* | 10/2010 | Menga | B25J 9/0006 601/34 |
| 2011/0066088 A1 | 3/2011 | Little et al. | |
| 2012/0172770 A1* | 7/2012 | Almesfer | B25J 9/0006 601/35 |
| 2012/0259429 A1 | 10/2012 | Han et al. | |
| 2013/0145530 A1 | 6/2013 | Mitra | |
| 2014/0257560 A1 | 9/2014 | Kamara | |
| 2015/0001269 A1* | 1/2015 | Sacksteder | B25J 9/0006 224/576 |
| 2015/0076196 A1* | 3/2015 | Brown | F16M 11/2014 224/271 |
| 2016/0089243 A1* | 3/2016 | Arun | A61F 2/644 623/20.14 |
| 2016/0146398 A1* | 5/2016 | Sitzmann | F16M 13/04 248/688 |
| 2017/0014993 A1* | 1/2017 | Barnes | B25J 19/0016 |
| 2017/0119132 A1* | 5/2017 | Pruess | A45F 3/08 |
| 2017/0196712 A1* | 7/2017 | Kazerooni | A61F 5/02 |
| 2017/0231856 A1 | 8/2017 | Karlovich | |

OTHER PUBLICATIONS

AIPOM Pokemon Papercraft. Jun. 2015. (Year: 2015).*
Orthocare 1. Orthocare Indonesia. Prosthetic Cases. Jul. 26, 2016 verified by the Wayback Machine. (Year: 2016).*
Orthocare 2. Orthocare Indonesia. Prosthetic Cases. Jul. 26, 2016 verified by the Wayback machine. (Year: 2016).*
"Shippo—wearable tail" retrieved on Aug. 25, 2017 from "http://neurowear.com/projects_detail/shippo.html".

* cited by examiner

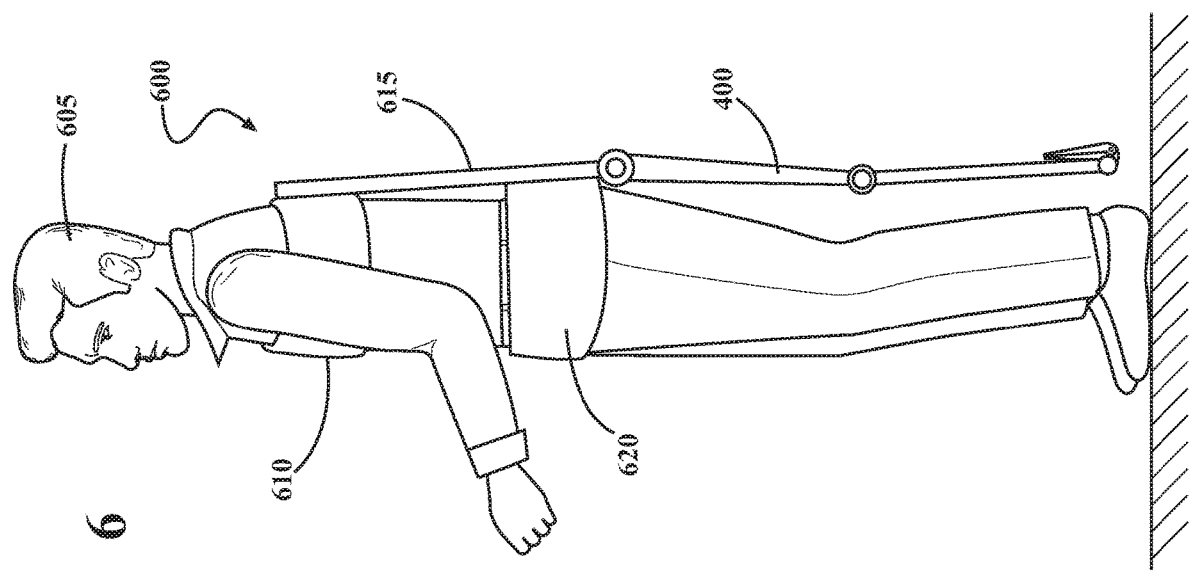
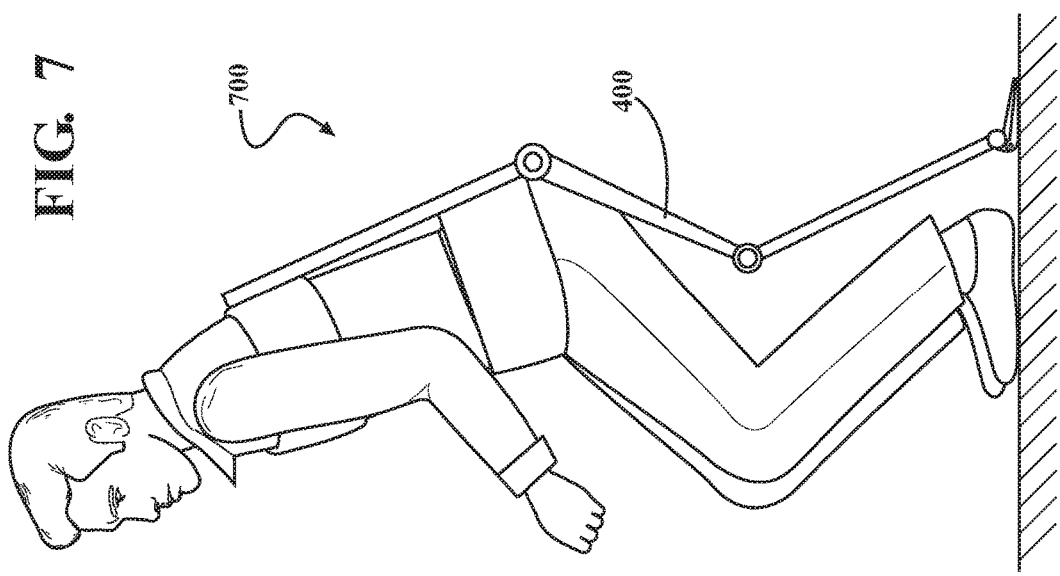

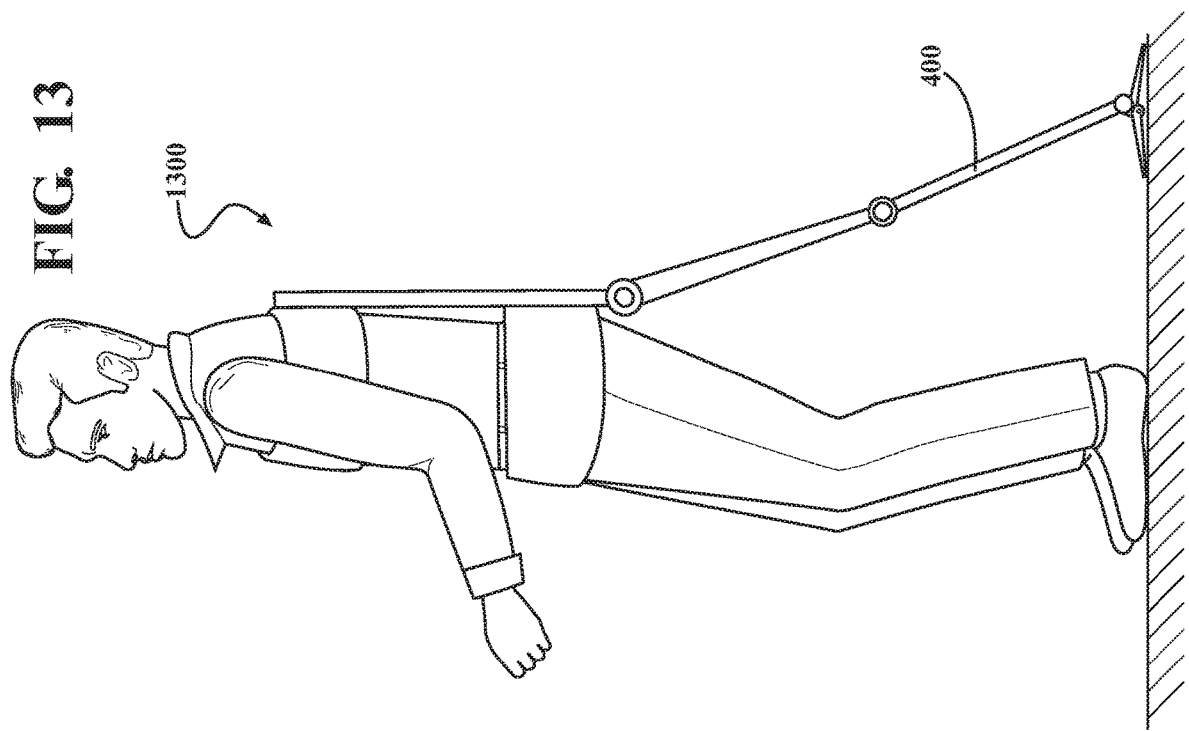
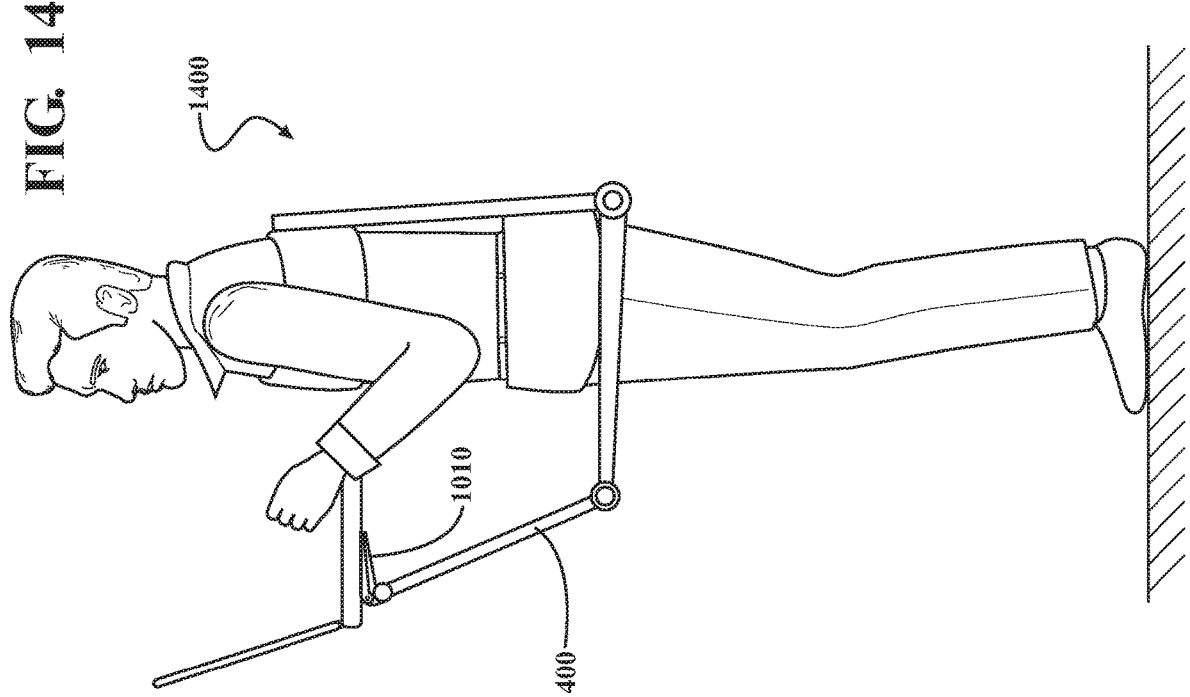

ARTIFICIAL LIMB FOR HOST ASSISTANCE

TECHNICAL FIELD

The subject matter described herein relates in general to an artificial limb and, more particularly, to a prosthetic tail that assists a host through improving mobility and supporting further tasks.

BACKGROUND

Injuries, diseases, aging, and other ailments can temporarily or permanently limit the mobility of individuals. The loss of mobility to an individual is one factor that can greatly affect general well-being beyond the specific ailments that cause the original mobility limitations. Present solutions for attempting to improve mobility are generally cumbersome and lack overall usability. For example, wheelchairs may improve mobility, in some circumstances, but are generally limited to uses in buildings and other areas that are handicap accessible, which generally do not include most residences. Moreover, even when a building is accessible to a wheelchair, often times aspects approaching the building such as curbs, stairs, vehicle access, and so on represent significant obstacles. Additionally, wheelchairs provide only seated positions for the user and do not provide support for upright positions, which further limits overall mobility.

Other devices designed to improve mobility such as crutches, canes, and walkers also present difficulties. For example, these devices are generally passive and, thus, rely on an individual's own sense of balance, which may be limited. Moreover, such devices also don't facilitate movement into an upright position or provide assistance with limitations to an individual's reach or support other movements. Accordingly, presently available devices that provide mobility assistance generally encounter limitations on usability.

SUMMARY

Example systems and methods are disclosed herein that relate to a mobility support device for facilitating movement of a host. For example, in one aspect, the present disclosure describes a prosthetic tail. The tail can be worn by a host and is generally secured to the host using at least a belt type of harness. In further aspects, the tail can also include a seat, a spinal support, a chest harness, and so on. In general, the tail can be used by individuals with a range of ailments. Therefore, the tail can include various configurations for supporting a host in order to ensure that the tail is sufficiently secure to provide the appropriate support.

The tail/limb itself can take multiple different forms. For example, in one approach, the limb is a fully articulated tail that is comprised of a plurality of tail members that resemble caudal vertebrae of an analog animal tail. That is, the limb includes a series of tail members resembling bones with each tail member being joined to an adjacent tail member at an integrated joint. In one embodiment, the joints between the tail members can be controlled to selectively articulate, and thus the limb can be controlled to move in at least one degree of freedom. In further aspects, the limb may be highly articulated, and the joints may provide for rotational movement through three degrees of freedom. Thus, the limb itself moves in a similar style as a feline or monkey tail. However, the limb generally functions to support the host through contacting the ground/floor and providing an upward and/or lateral force to the host. Thus, the limb extends from the host at a lower back or base of the spine area to the floor.

In further aspects, instead of being constructed from the tail members, the limb is comprised of two or more joints connected via supporting members. Thus, by way of analogy, the limb may resemble more of a human arm than a tail. However, the limb is still attached near a base of the spine. In such a case, the limb is comprised of at least, for example, a base joint, a base member, a mid-joint, and a lower member. Continuing with the arm analogy, the base joint generally corresponds to a shoulder joint, the base member generally corresponds to an upper arm, the mid-joint generally corresponds to an elbow, and the lower member generally corresponds to the forearm. Of course, while the limb is described in the context of an arm, the limb is, nevertheless, attached at the base of the spine of the host in order to provide support with standing, sitting, and walking movements. As a further aspect, the disclosed joints can include ratcheting mechanisms to provide for a mechanical means of extending the limb and exerting an upward force on the host while resisting folding/flexing movement.

Moreover, in further aspects, the limb folds and stows against a back of the host. Additionally, the limb can be controlled to assist with holding items for the host such as drinks, laptops, and so on. Furthermore, the limb can maneuver to reach items out of a reach of the host. In either case, additional aspects of the limb include, in one embodiment, hydraulic controls for movement of the limb, electronic controls for movement of the limb, a processor and control modules, and other aspects related to providing powered control of the limb. In one embodiment, the mobility system includes sensors that provide real-time information for controlling the limb. For example, the mobility system can acquire the sensor data and then analyze the sensor data to identify assistance events, which are occurrences within the surrounding environment relating to the movement of the host for which the host may need assistance in moving. Thus, as the mobility system anticipates the assistance events, the mobility system identifies assistance movements for the limb that improve movement of the host. The assistance movements can include such maneuvers as extending the limb to provide upward force and facilitate standing, moving in a particular direction to improve the balance of the host, assisting with downward sitting movements, and so on. Alternatively, or additionally, the mobility system can execute movements at the request of the user that are requested via voice, gesture or another input method. In either case, the disclosed limb provides for improving the mobility of the host through supporting the host and providing assistance in moving.

In one embodiment, a mobility system for improving the mobility of a user is disclosed. The mobility system includes a support component including at least a waist device that is configured to secure the system to the user at a waist area of the user. The mobility system includes a limb attached to the support component and extendable from the support component to a floor when the user is in a standing position. The limb is configured to support the user by providing a rigid structure between the floor and the user. The limb is configured to assist the user in transitioning from a seated position to the standing position by applying a substantially upward force to the user through the support component when transitioning to the standing position.

In one embodiment, a method of improving mobility of a user through use of a prosthetic limb attached to the user is disclosed. The method includes collecting environmental sensor data about surroundings of the user and movement sensor data about a present position and trajectory of the user. The method includes analyzing the environmental sensor data and the movement sensor data to determine whether an assistance event for actively assisting the user is imminent. The method includes identifying an assistance movement for the limb associated with the assistance event. The method includes controlling the limb to maneuver according to the assistance movement to assist the user and improve mobility of the user.

In one embodiment, a prosthetic device for improving mobility of a user is disclosed. The prosthetic device includes a support component including at least a waist device that is configured to secure the prosthetic device to the user at a waist area of the user. The prosthetic device includes a limb attached to the support component. The limb includes a base joint that is connected with the support component and that is configured to pivot through at least one degree of freedom in order to move the limb toward and away from the user. The limb includes a base member connected with a pivoting point of the base joint. The base member is a rigid structure extending from the base joint. The limb includes a mid-joint that is connected with a distal end of the base member away from the pivoting point of the base joint. The mid-joint is configured to pivot through at least one degree of freedom that includes a same plane of movement as the base joint. The limb includes a lower member that is a rigid structure connected with the mid-joint and extending from the mid-joint such that the lower member pivots about the mid-joint. The limb is configured to support the user by providing a rigid structure between the floor and the user. The limb is configured to assist the user in transitioning from a seated position to the standing position by applying a substantially upward force to the user through the support component when transitioning to the standing position.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments, one element may be designed as multiple elements or multiple elements may be designed as one element. In some embodiments, an element shown as an internal component of another element may be implemented as an external component and vice versa. Furthermore, elements may not be drawn to scale.

FIG. 6 is an example view of a limb in an extended position.

FIG. 7 is an example view of a limb assisting a user with transitioning into a standing position.

FIG. 13 is an example view of a limb assisting a user with resting/leaning while standing.

FIG. 14 is an example view of a limb holding a laptop computer for a user.

DETAILED DESCRIPTION

Figure 1:
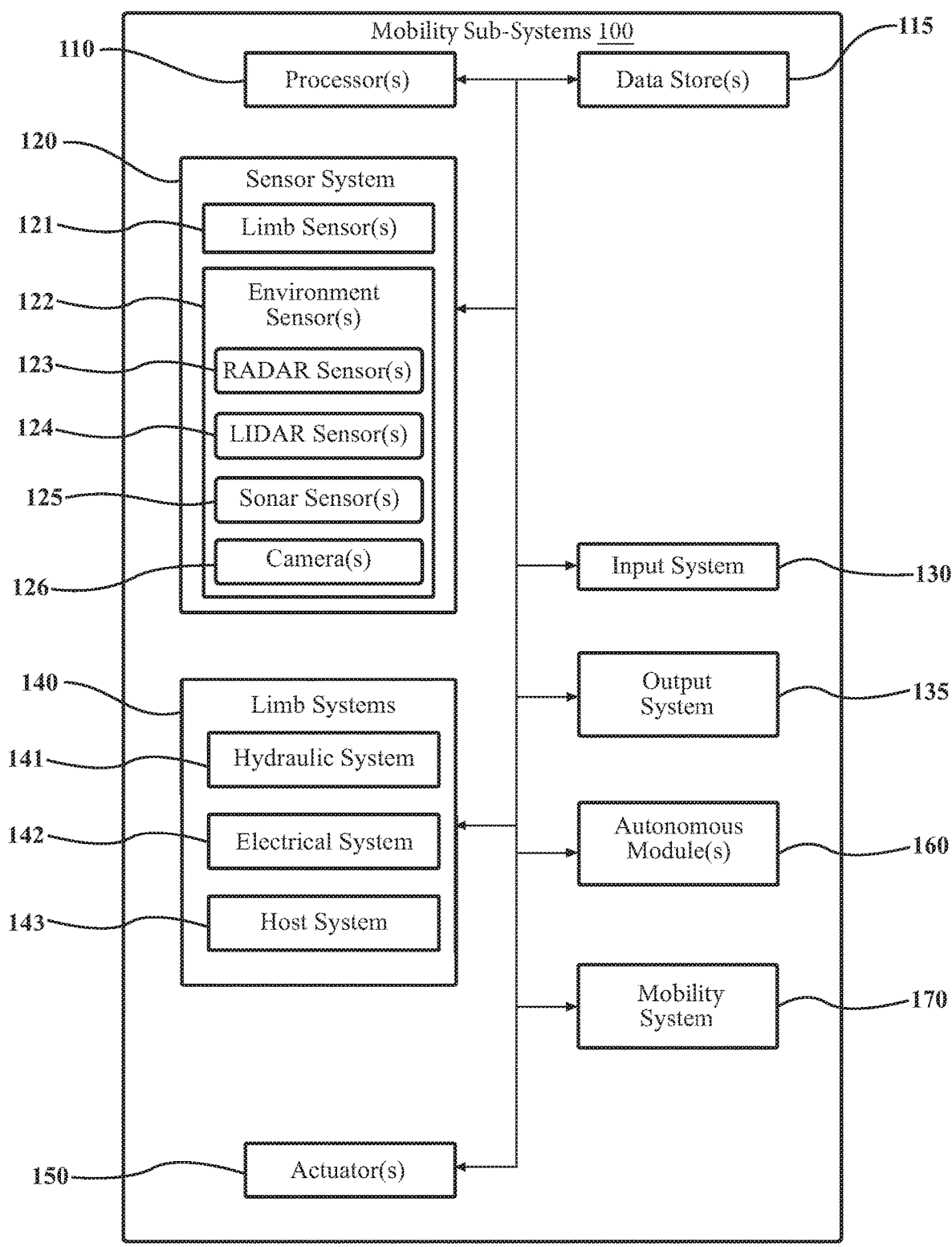
FIG. 1 illustrates one embodiment of mobility sub-systems that may be implemented in support of a mobility system.

Systems, methods and other embodiments associated with improving the mobility of a user via an attached prosthetic limb are disclosed herein. As mentioned previously, wheelchairs and other mobility assistance devices for individuals with ailments and other mobility limitations are limited by an extent to which the noted devices can assist an individual. That is, for example, the particular devices are generally focused on helping the individual move between locations while otherwise not considering additional aspects such as standing, reaching, balance, and so on. Moreover, as one example, while wheelchairs can assist with moving around a location, the location itself must generally be wheelchair accessible and thus accessing the location can present difficulties for wheelchairs.

Accordingly, in one embodiment, a mobility system includes a prosthetic limb that attaches to a host/user and provides assistance in the form of support when transitioning between sitting and standing positions. In general, the prosthetic limb attaches to the user at the base of the spine of the user in a location reminiscent of a tail. Thus, by way of analogy, the limb may be thought of as a prosthetic tail. Accordingly, in various embodiments, the limb can be implemented in different forms. For example, the limb can have many independent tail members akin to caudal vertebrae of an animal tail.

In an alternative implementation, the limb may have fewer joints (e.g., 2-3) and be formed from fewer structural members (e.g., 2-3). Accordingly, the limb may have a form that is similar to an arm. In either case, the limb of the mobility system is implemented to provide mobility assistance to a user through providing support and/or assistive force in the movement for a user transitioning between a seated position and a standing position. Moreover, the mobility system, in one embodiment, provides balance support by, for example, generating movements of the limb to counteract imbalance. In still further aspects, the limb provides a simple support for a user to rest when standing.

Additionally, the limb can be implemented to provide for active assistance by anticipating trips, falls, and other movements for which the limb can maneuver in a manner so as to avert a fall, or at least mitigate a potential hazard. In further aspects, the mobility system controls the limb to provide grasping assistance through reaching and grabbing overhead items, holding items, carrying items, and so on. In this way, the limb is implemented to improve mobility of a user through dynamic assistance with various tasks while avoiding difficulties of the existing modes of assistance as previously outlined.

The mobility system achieves the noted benefits through multiple different possible configurations. For example, the limb can be implemented as a passive system using manual mechanically ratcheting joints in one approach. By contrast, in further approaches, the limb can include powered movement through hydraulic mechanisms, pneumatic mechanisms, and/or electric motors. Moreover, the mobility system can include an array of sensors for detecting aspects of a surrounding environment and aspects of the host (e.g., balance, trajectory, etc.). In still further aspects, the mobility system can include active grasping mechanisms, attachments for holding objects, and so on. Thus, the mobility system leverages many different aspects of the limb in order to improve mobility of a user.

Referring to FIG. 1, an example of mobility sub-systems 100 for a prosthetic limb are illustrated. While arrangements will be described herein with respect to the mobility system 170 and the sub-systems 100, it will be understood that embodiments are not limited to the noted arrangement of the sub-systems 100. In some implementations, the sub-systems 100 may be any arrangement of components that, for example, may be needed to implement the noted aspects.

It will be understood that in various embodiments it may not be necessary for the sub-systems 100 to include all of the elements shown in FIG. 1. The sub-systems 100 can have any combination of the various elements shown in FIG. 1. Further, the sub-systems 100 can have additional elements to those shown in FIG. 1. In some arrangements, the sub-systems 100 may be implemented without one or more of the elements shown in FIG. 1. Further, while the various elements are shown as being located within the sub-systems 100 in FIG. 1, it will be understood that one or more of these elements can be located external to the sub-systems 100. Further, the elements shown may be physically separated by large distances.

Some of the possible elements of the sub-systems 100 are shown in FIG. 1 and will be described along with subsequent figures. However, a description of many of the elements in FIG. 1 will be provided after the discussion of FIGS. 2-14 for purposes of brevity of this description. Additionally, it will be appreciated that for simplicity and clarity of illustration, where appropriate, reference numerals have been repeated among the different figures to indicate corresponding or analogous elements. In addition, the discussion outlines numerous specific details to provide a thorough understanding of the embodiments described herein. Those of skill in the art, however, will understand that the embodiments described herein may be practiced using various combinations of these elements.

In either case, the sub-systems 100 include the mobility system 170 that is implemented to perform methods and other functions as disclosed herein relating improving mobility of a user through use of an additional prosthetic limb (e.g., tail). The noted functions and methods will become more apparent with a further discussion of the figures. As an initial note, a structure of the limb is discussed subsequent to the functional aspects of the system and method of FIGS. 2 and 3. However, it should be appreciated that the disclosed functionality is generally applicable to the separate forms of the limb as will be discussed subsequently.

Figure 2:
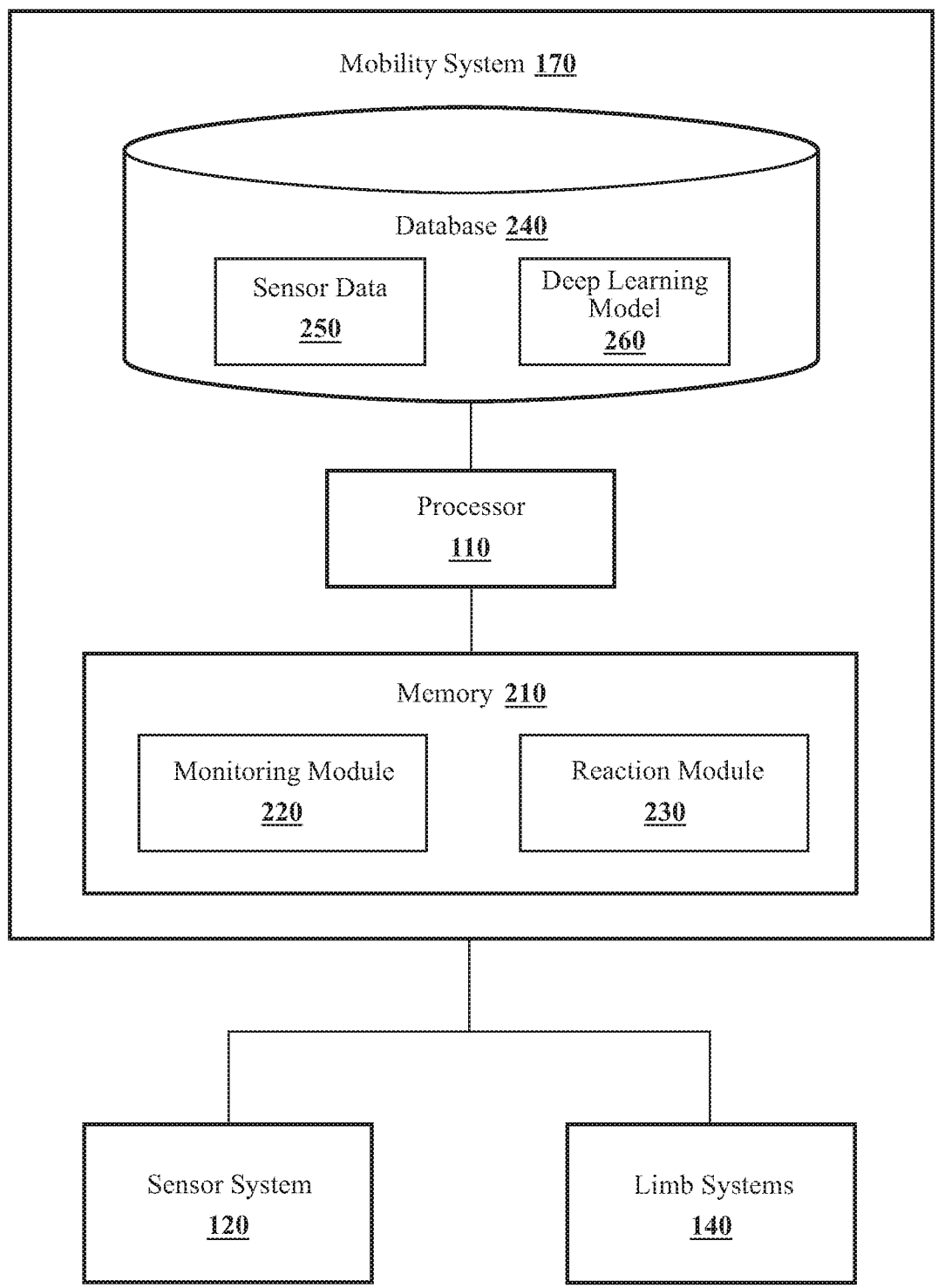
FIG. 2 illustrates one embodiment of a mobility system that is associated with improving the mobility of a user.

With reference to FIG. 2, one embodiment of the mobility system 170 of FIG. 1 is further illustrated. The mobility system 170 is shown as including a processor 110 from the sub-systems 100 of FIG. 1. Accordingly, the processor 110 may be a part of the mobility system 170, the mobility system 170 may include a separate processor from the processor 110 of the sub-systems 100 or the mobility system 170 may access the processor 110 through a data bus or another communication path. In either case, the processor 110 is illustrated as part of the mobility system 170 for purposes of explanation. Additionally, in one embodiment, the mobility system 170 includes a memory 210 that stores a monitoring module 220 and a reaction module 230. The memory 210 is a random-access memory (RAM), read-only memory (ROM), a hard-disk drive, a flash memory, or other suitable memory for storing the modules 220 and 230. The modules 220 and 230 are, for example, computer-readable instructions that when executed by the processor 110 cause the processor 110 to perform the various functions disclosed herein.

Accordingly, in one embodiment, the monitoring module 220 generally includes instructions that function to control the processor 110 to acquire sensor data 250. As an initial note, as used herein sensor data 250 is used to generally refer to both environmental sensor data and movement sensor data. Thus, the monitoring module 220 generally acquires the sensor data 250 from a camera 126, a sonar 125, a LIDAR 124, a radar 123, and/or another sensor integrated with the sub-systems 100. Moreover, the monitoring module 220 may also acquire information from an IMU, one or more gyros, host monitoring sensors (e.g., heart rate monitors, etc.), extremity tracking sensors that indicate host extremity position information (e.g., arm positions, leg positions, etc.), information from a mobile phone or other device in use by a host, and so on. In further aspects, the monitoring module 220 controls multiple ones of the noted sensors that are embedded with the sub-systems 100.

In either case, the monitoring module 220 collects and stores the two sets of data as the sensor data 250 in database 240. The database 240 is, for example, an electronic data structure stored in the memory 210 or another electronic data store and that is configured with routines that can be executed by the processor 110 for analyzing stored data, providing stored data, organizing stored data, and so on. Thus, in one embodiment, the database 240 stores data used/provided by the modules 220 and 230 in executing various functions. In one embodiment, the database 240 includes the sensor data 250 and a deep learning model 260. Additionally, while the sensor data 250 and the deep learning model 260 are illustrated as being stored within the database 240, it should be understood that in various embodiments the sensor data 250 and/or the deep learning model 260 can be stored in the memory 210, integrated within one or more data structures of the monitoring module 220 and/or the reaction module 230, and so on.

In either case, the monitoring module 220 generally includes computer-executable instructions to analyze the sensor data 250 using the deep learning model 260. Accordingly, the monitoring module 220, in one embodiment, provides the sensor data 250 as an electronic input into the deep learning algorithm 260 which produces an indication about whether an assistance event for actively assisting the user is imminent. That is, the deep learning algorithm 260 correlates the provided sensor data 250 to determine whether the limb should be controlled to assist the user. By way of example, the monitoring module 220 can implement the deep learning model 260 to identify when the user is attempting to transition into a standing position, into a seated position, leaning to relax, is off-balance, needs assistance with relieving weight from a leg during locomotion, or any other circumstance for which the limb is capable of providing assistance.

As for the deep learning algorithm 260 itself, the monitoring module 220 includes routines, data structures, data and other aspects that implement the deep learning algorithm 260. Thus, in one or more embodiments, the deep learning algorithm 260 is at least partially embodied by instructions of the monitoring module 220. Furthermore, the deep learning algorithm 260 is, for example, a convolutional neural network (CNN), a recurrent neural network (RNN), a long short-term memory (LSTM) neural network, or another suitable machine learning approach that can use the sensor data 250 to characterize movements of the user, aspects of the surroundings, and other factors to determine an imminence of a particular assistance event.

Thus, in one embodiment, the monitoring module 220 feeds the sensor data 250 into the deep learning algorithm 260 in order to generate a determination of an assistance event as an output. Moreover, the reaction module 230 generally includes computer-executable instructions to identify from the determined assistance event an assistance movement for the limb that improves mobility of the user. Thus, the reaction module 230, in one embodiment, identifies an assistance movement that correlates with the assistance event. In one embodiment, the assistance movement is a movement of the limb that facilitates mobility of the user.

For example, the assistance movement can include extending the limb to push upward against the user to facilitate transitioning to a standing position, slowly releasing tension from an extended position to a retracted position to facilitate sitting, locking in a fully extended configuration to provide a leaning support, tracking one leg to relieve weight from the leg when walking/standing, moving to improve balance, moving to mitigate a trip or a fall, and so on. Moreover, the mobility system 170 can control the limb to execute secondary assistance movements such as reaching overheard to grasp objects for the user, reaching around to hold objects in front of the user, pushing objects (e.g., doors) in front of the user, and so on.

Figure 3:
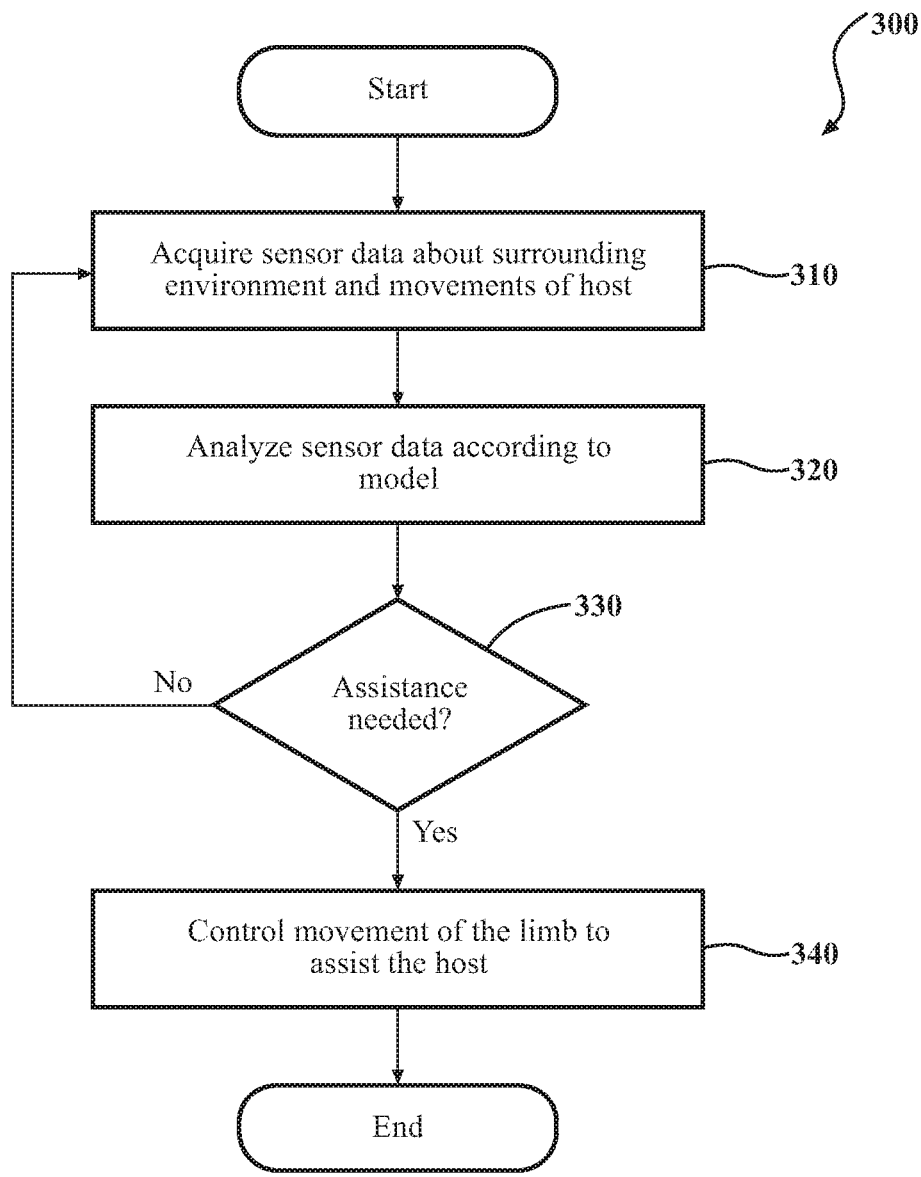
FIG. 3 illustrates a flow diagram of a method that is associated with controlling a prosthetic limb to improve the mobility of a user.

Additional aspects of controlling the limb will be discussed in relation to FIG. 3. FIG. 3 illustrates a flowchart of a method 300 that is associated with using audio data to identify objects. Method 300 will be discussed from the perspective of the mobility system 170 of FIGS. 1 and 2. While method 300 is discussed in combination with the mobility system 170, it should be understood that the method 300 is not limited to being implemented within the mobility system 170, but is instead one example of a system that may implement the method 300.

At 310, the monitoring module 220 collects environmental sensor data about surroundings of the user and movement sensor data about a present position and trajectory of the user. In one embodiment, the monitoring module 220 stores the collected information as the sensor data 250 in the database 240 or another suitable electronic data store. In general, the monitoring module 220 controls sensors of the sensor system 120 to collect the sensor data 250. In further aspects, the monitoring module 220 communicates with secondary or remote sensors that are not directly controlled or integrated with the limb. For example, the monitoring module 220 communicates with a mobile smartphone of the user to acquire information from sensors within the smartphone about the user and the surroundings. Additionally, the monitoring module 220 can acquire information from other devices of the user such as smartwatches, fitness sensors, head-mounted displays (e.g., glasses), heart rate monitors, and so on. In general, the monitoring module 220 functions to acquire any available information in real-time that can further inform awareness about the user and a surrounding environment of the user. Thus, whether sensors are integrated with the limb as in the case of the limb sensors 121 and the environment sensors 122 or are remote from the limb but can provide useful information, then the monitoring module 220 can acquire the information in order to improve the analysis as discussed subsequently.

At 320, the monitoring module 220 analyzes the environmental sensor data and the movement sensor data to determine whether an assistance event for actively assisting the user is imminent. In one embodiment, the monitoring module 220 analyzes the sensor data 250 to determine the presence of obstacles and other features surrounding the user that affect an ability of the user to move. Thus, the monitoring module 220, for example, analyzes the sensor data 250 to characterize movements of the user and to anticipate when the user may need to be assisted. The monitoring module 220, in one embodiment, can characterize the sensor data 250 to determine an occurrence of circumstances that define an assistance event. An assistance event can include many different types of events but generally includes circumstances that influence the mobility of the user.

By way of example, the assistance event can include changing positions between seated and standing, walking up stairs, walking down stairs, bending at a waist, reaching, leaning, tripping, and so on. Moreover, additional assistance events can include providing assistance to the user through grasping items, shifting weight from an injured leg, holding objects, opening doors, reaching for objects overhead, and so on. Thus, at least some of the movements of the limb can be initiated through an active control signal provided by the user.

In either case, the monitoring module 220 analyzes the sensor data 250, in one embodiment, using a deep learning model 260 or other machine learning model that indicates when the assistance event is imminent. Thus, the monitoring module 220 can determine when an assistance event is to occur or is occurring by using the deep learning model 260 to characterize the sensor data 250.

At 330, the reaction module 230 determines whether a resulting analysis of the sensor data 250 indicates an assistance event. If there is no assistance event, then the mobility system 170 continues to monitor for an occurrence. However, if the reaction module 230 determines that results of the previous analysis at 320 indicate an assistance event is occurring or about to occur, then the reaction module 230 proceeds at 330 by, for example, identifying an assistance movement for the limb associated with the assistance event. In one aspect, the monitoring module 220 may indicate which movement is appropriate for the particular assistance event or aspects of the assistance event that are relevant to the assistance movement (e.g., a location of an obstacle, etc.).

Thus, the reaction module 230, in one aspect, uses at least an identifier of the assistance event to lookup a corresponding assistance movement. In further aspects, the reaction module 230 can also provide additional information such as a present trajectory, and so on in order to identify the particular assistance movement that is to be executed. In a further aspect, the reaction module 230 simply monitors for a control signal from the user to initiate a movement. For example, the reaction module 230 can detect when a user performs a particular gesture indicating a desired movement, provides voice inputs specifying a movement, provides control inputs through an input system 130, provides wireless communications via a remote interface on a mobile phone or other device indicating a movement, and so on.

At 340, the reaction module 230 controls the limb to maneuver according to the assistance movement. In one embodiment, the reaction module 230 provides electronic control signals to electric motors, hydraulic valves/pumps, and/or other components that cause the limb to move in accordance with the assistance maneuver.

As previously noted, the assistance movements can generally include any movements of the limb that support mobility of the user. Thus, the assistance movements generally include movements similar to a cane or other support device in addition to more active assistance movements such as actively providing an upward force for transitioning into a standing position, providing support when transitioning to a seated position, providing balance support, securing a user through grasping handrails, and so on. In this way, the mobility system 170 improves the mobility of the user through controlling the limb to actively assist the user.

Figure 4:
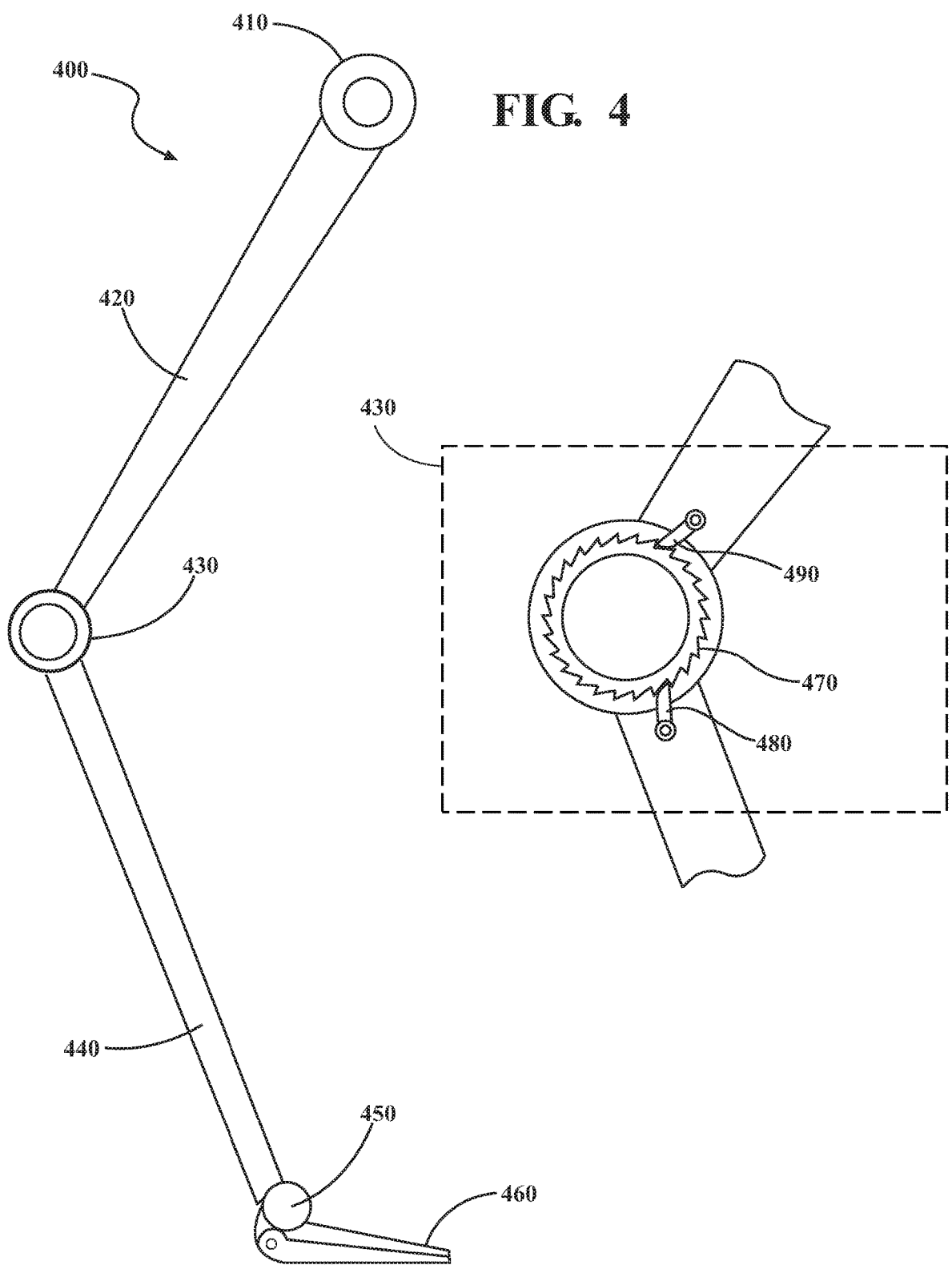
FIG. 4 is a diagram of one embodiment of a limb.

Attention will now be provided to the structure of the limb along with different configurations of the limb and the mobility system 170. Accordingly, FIG. 4 illustrates one embodiment of a limb 400 that is associated with improving mobility of a user. The limb 400 is one example of a limb that can be implemented with the mobility system 170. In FIG. 4, the limb 400 is illustrated in isolation without additional aspects of the mobility system 170 such as a support component. In either case, the limb 400 includes a base joint 410, a base member 420, a mid-joint 430, a lower member 440, a lower joint 450, and a foot 460.

In general, the base joint 410 is connected with the noted support component which is not illustrated, but also provides for movement of the limb 400 in a rotational manner toward and away from the user. Thus, the base joint 410 provides for rotating the limb 400 in an arc behind the user. The base member 420 extends from the base joint 410 to the mid-joint 430 and provides rigid support therebetween. Moreover, in one or more implementations, the base member 420 is hollow and serves as a conduit for carrying electrical connections, hydraulic connections, and other such utility aspects between components of the limb 400.

The mid-joint 430 generally functions in a similar manner as the base joint 410. A zoomed cross-sectional view of the mid-joint is also provided along with FIG. 4. As illustrated, the mid-joint 430 includes a gear 470 that is engaged by the base member 420 and the lower member 440 via respective pawls 480 and 490. In general, the gear 470 and the pawls 480 and 490 make up a ratcheting mechanism of the mid-joint 430. While illustrated with two pawls 480 and 490, in further aspects, the ratcheting mechanism may include just one of the pawls 480 and 490. The ratcheting mechanism is one example of a mechanical joint that is implemented in the base joint 410, the mid-joint 430, and the lower joint 450 in various implementations. Of course, the joints 410, 430, and 450, in further embodiments, can also be implemented using different types of joints. As an additional aspect, the joints 410, 430, 450 can include springs to resist flexion and facilitate extension.

Moreover, the joints 410, 430, 450 can be manually controlled to release and ratchet via, for example, a pull cable. In further aspects, the joints 410, 430, 450 can be electronically controlled via the mobility system 170 and thus the ratchet, for example, can act as a safety mechanism. As an additional note, while the joints 410, 430, and 450, are generally discussed as moving through one degree of freedom that includes a plane of movement perpendicular to the user, the joints 410, 430, and 450, in one embodiment, pivot through two or more degrees of freedom to provide a greater range of motion. Moreover, the joints 410, 430, and 450 may pivot in different degrees of freedom in one more embodiments. Furthermore, the limb 400 includes the lower member 440 extending from the mid-joint 430. The lower member 440 is similar in construction to base member 420. That is, the lower member 440 is, for example, also hollow.

As a further matter, the base member 420 and the lower member 440 may have a generally cylindrical shape. Additionally, the limb 400 and primarily the members 420, 440, and 460 are comprised of lightweight materials such as carbon fiber, an alloy metal, a composite material, or another material or combination of materials that are lightweight and provide appropriate strength to support the user. Continuing with the limb 400, the lower member 440 is connected with the lower joint 450. The lower joint 450 connects with the foot 460. The foot 460, in one embodiment, braces the limb 400 against the ground/floor. Thus, the foot 460 may include a non-slip coating where the foot 460 interfaces with the ground to provide the limb 400 from slipping out from under the user.

In further aspects that will be discussed in greater detail subsequently, the foot 460 includes attachment points for modular attachments such as wider feet, a grasper, trays, or other structures. Moreover, the foot 460 may also include an integrated grasper that is configured through the foot 460 splitting into two separate halves.

Figure 5:
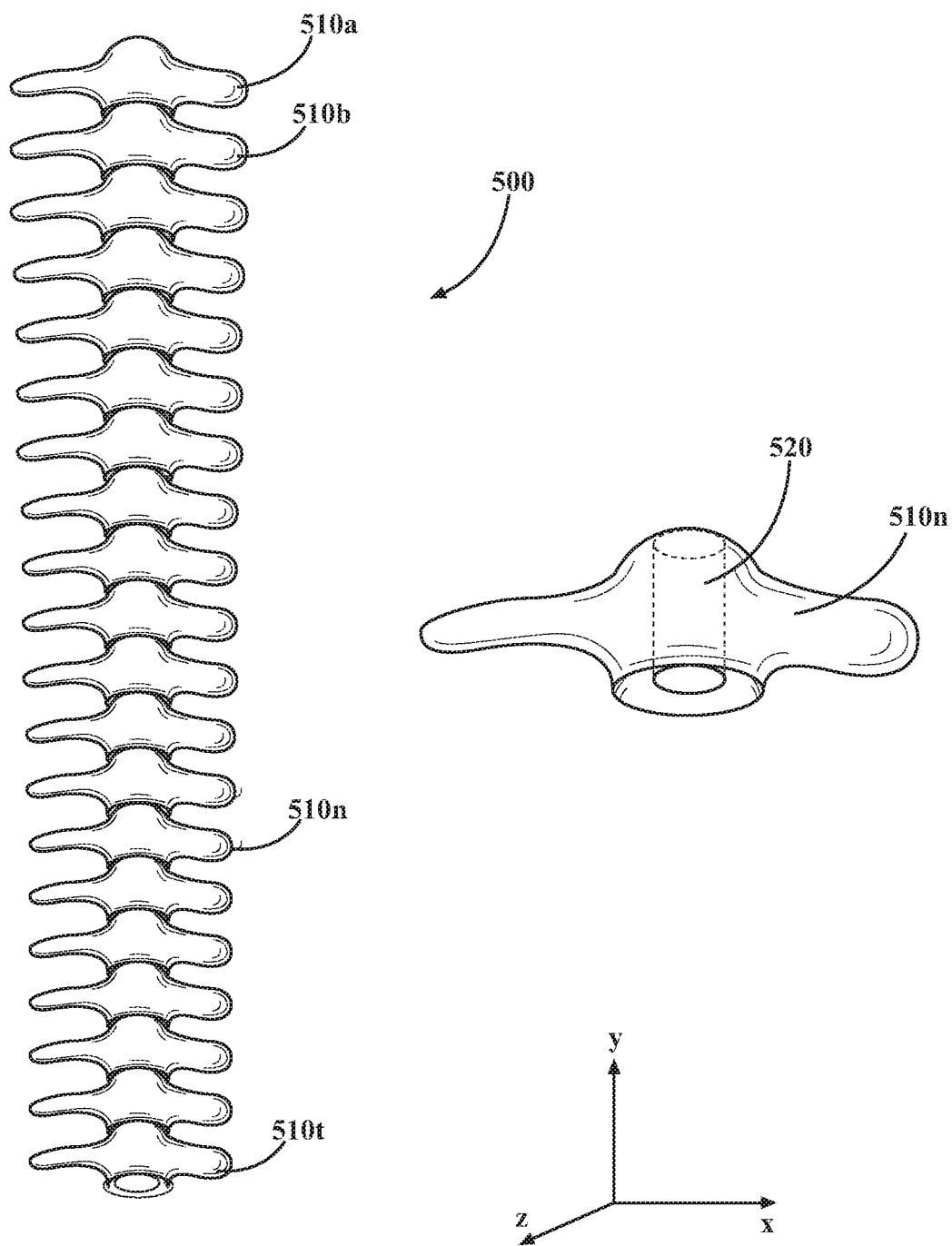
FIG. 5 is a diagram of another embodiment of a limb that is comprised of a plurality of tail members.

Continuing with various implementations of the limb, FIG. 5 illustrates an articulated limb 500. As an initial matter, it should be noted that the limb 500 is illustrated in part and has omitted a connection point with a support component that attaches to the user and also a foot (i.e., foot 460) or other end attachment. In either case, the limb 500 can generally be substituted for elements 410-450 of the limb 400. The articulated limb 500 includes a plurality of tail members 510a-t. As shown, the limb 500 includes approximately twenty tail members but may include a different number (e.g., more or fewer) depending on a particular implementation.

In either case, the tail members 510 are connected together at integrated joints that generally provide for multiple degrees of freedom in movement. Accordingly, the tail 500 can move through multiple planes in addition to the X-Y plane of the limb 400. For example, because each of the tail members 510 can articulate in multiple different directions independently, the tail 500 can be controlled to move with a high dexterity to perform many different tasks. Thus, the tail 500 can move around the user to hold objects, and perform other tasks while also providing for assistance with transitioning between standing and sitting. Moreover, the tail 500 can form additional shapes (e.g., semi-circular) using the freedom of movement from the joints in order to hold objects, and so on.

While not explicitly illustrated, the tail 500 can be controlled via membranes at the interface of each of the tail members 510 that are part of the noted integrated joints. For example, the membranes can be controlled using hydraulics routed through the cavity 520 or via another mechanism to selectively adjust the membranes (e.g., inflate, rotate, etc.) in a particular way (e.g., asymmetric) to induce movement in the limb 500. In further aspects, the cavity 520 may provide a route for tensioning cables or another mechanism that can be routed to different ones of the tail members 510 and selectively tensioned to induce movement.

The mechanical systems for controlling the limb 400 and the limb 500, in one embodiment, are routed through the support component and housed in a structure on the back of the user or within the support component itself. It should be appreciated that providing accommodations for batteries, hydraulic components, electronic computing components, sensors, and/or other utilities of the limb can take many forms. However, the focus of the present disclosure is the functionality provided by the implemented tail and thus are not explicitly detailed herein.

However, FIGS. 6-14 illustrate further aspects about how the mobility system 170 functions and thus will now be described as exemplary embodiments of how the limb 400 may be implemented. FIG. 6 illustrates an example view 600 of a user 605 wearing the mobility system 170 that is configured with the limb 400. In the view 600, the limb 400 is illustrated in a ready position and can be controlled to maneuver upon detecting an assistance event as previously explained. In either case, the view 600 shows how the limb 400 can be secured to the user 605 through a chest harness 610 and a waist device 620 that is, for example, a belt. The waist device 620 may also include a seat in order to support the weight of the user 605 without chaffing or otherwise stressing areas of the user 605 associated with the other support components.

The configuration of FIG. 6 also depicts a spinal support 615 that is a rigid member connecting the chest harness 610 and the waist device 620. The spinal support 615 is, for example, constructed of a material similar to the members 420 and 440 of the limb 400. The spinal support 615 may have a shape that is cylindrical, flat or another suitable shape. It should be noted that considerations for the shape of the spinal support 615 include strength and similar considerations as the other members, but also includes aspects relating to the comfort of the user 605 since the user 605 will rest against the spinal support 615 when seated. Consequently, the support 615 may be flattened, padded, or include other aspects to facilitate comfort. In either case, the support component is configured to attach the limb 400 midway on the back of the user at, for example, the base of the spine thereby attaching the single limb to the user without attachment to a leg or other portion of the lower extremities and in isolation without separate structures for each leg.

Figure 8:
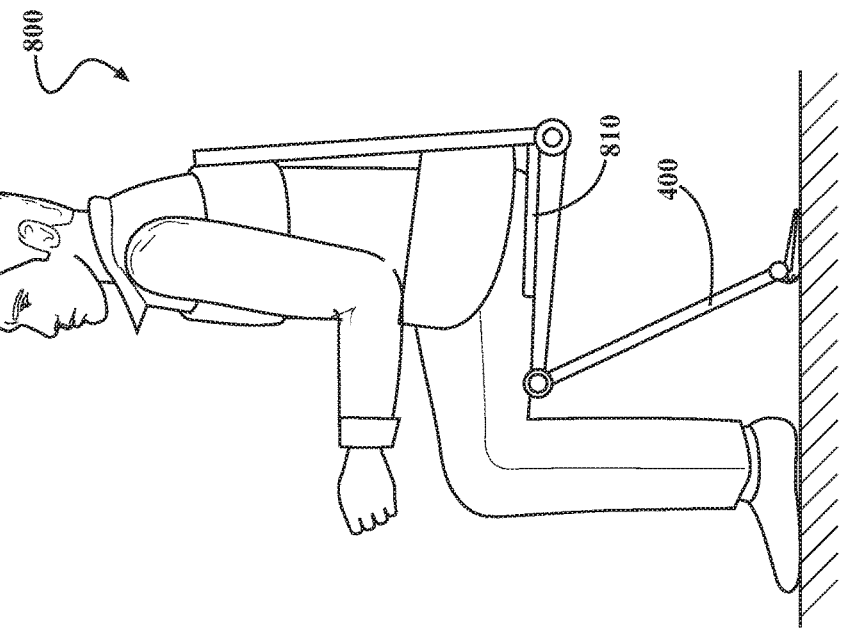
FIG. 8 is an example view of a limb with a user in a seated position.

FIG. 7 illustrates a view 700 of the limb 400 with the user transitioning between a seated and a standing position. As seen in the view 700, the foot 460 is planted on the ground while the joints 410, 430, and 450 assist the user with transitioning by providing support through either the plain mechanical ratcheting, as previously discussed, or through a power-assisted movement. FIG. 8 illustrates a view 800 of the mobility system 170 with the limb 400. As shown, the base joint 410 includes a seat 810 attached thereto as part of the support component. Thus, the seat 810 may extend between the legs of the user to provide support. Moreover, while the limb 400 is shown in a chair-type of configuration, in general, the limb 400 is itself not used as a chair/seat but instead is configured in the shown manner when the user is seated on a couch, chair, or another piece of furniture. Thus, as the user moves to stand, the limb 400 can provide an upward force to assist in the movement.

Figure 9:
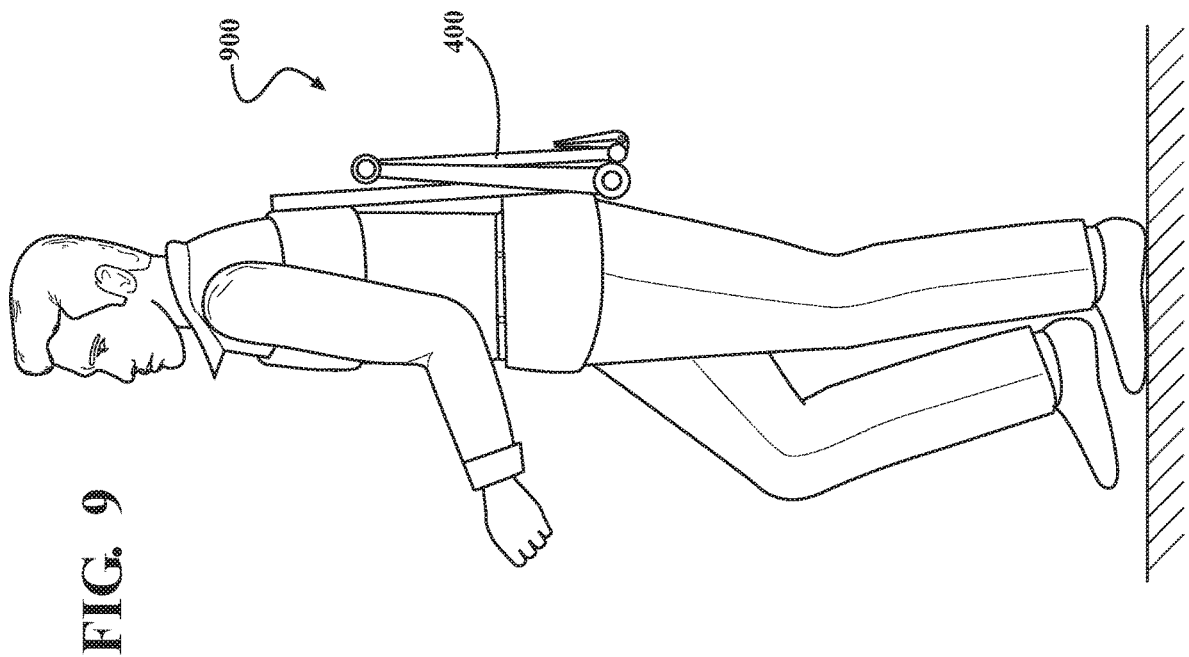
FIG. 9 is an example view of a limb in a stowed position on a back of a user.

FIG. 9 includes a view 900 of the user 605 in which the limb 400 is in a stowed position on the back of the user 605. The stowed position is useful when, for example, the user 605 is upright and does not require assistance with movement. Of course, depending on the particular user, the limb may be kept in a ready state as shown in FIG. 6 in order to maintain the limb 400 at the ready instead of being in a standby mode as shown in FIG. 9.

Figure 10:
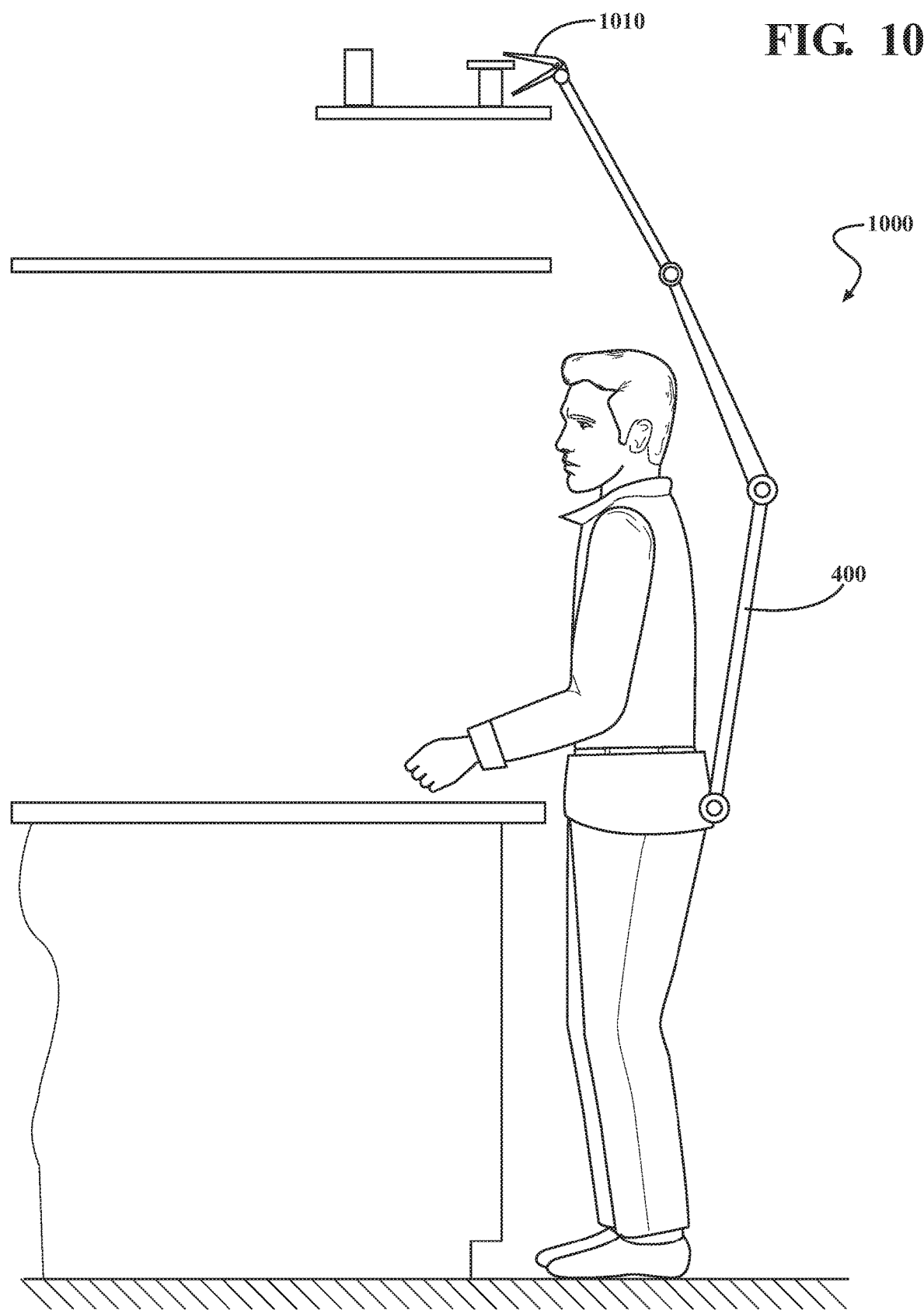
FIG. 10 is an example view of a limb assisting a user with reaching an overhead object.

FIG. 10 illustrates a further view 1000 in which the limb 400 is pivoted into an overhead configuration in order to grasp objects using graspers 1010 that are, for example, integrated within the foot 460. Moreover, it should be noted that the configuration of the limb 400 shown in FIG. 10 includes an additional support member between the lower member 440 and the base member 420. Thus, the limb 400 can be configured with additional sections in order to provide additional overall length. Alternatively, the additional sections may nest inside one another and extend when needed to provide a more compact configuration.

Figure 11:
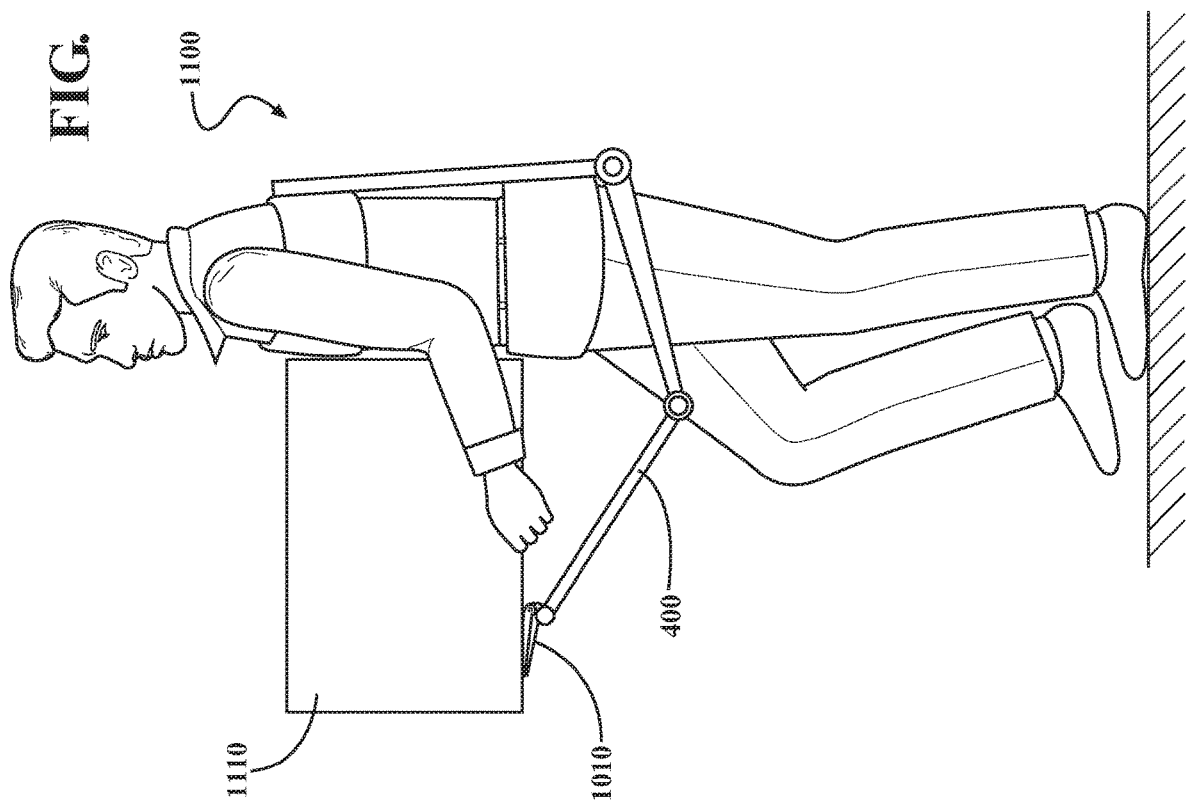
FIG. 11 is an example view of a limb assisting a user with holding an object.

FIG. 11 illustrates a further view 1100 in which the limb is rotated to a front side of the user and the grasper 1010 is assisting the user with holding an object 1110. Thus, the limb 400 may also assist with holding objects and with transferring weight to a more efficient carrying configuration. Additionally, as shown in FIG. 11 the limb 400 rotates around the user instead of extending through the legs of the user. Thus, the base joint 410 in this configuration is, for example, configuration to slide on the support component or otherwise rotate in a manner so as to permit limb 400 to move around the user. Thus, the base joint 410, in the illustrated example, includes additional rotation through more than a single degree of freedom in order to facilitate the illustrated movement.

Figure 12:
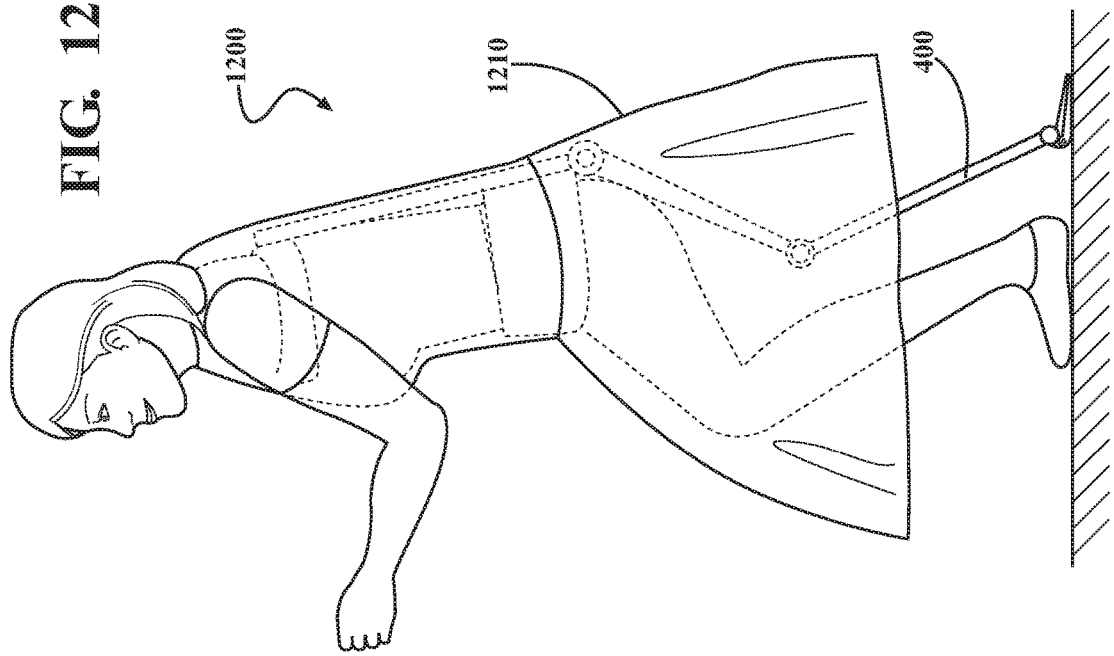
FIG. 12 is an example view of a limb configured underneath clothing of a user.

FIG. 12 illustrates a view 1200 in which the mobility system 170 when configured with the limb 400 is worn in a configuration so as to be at least partially concealed from view. In this noted configuration, the system 170 is provided under clothes 1210 of the user, in particular, under a dress. It should be noted that in such a configuration some movements such as overhead movements may be limited in order to prevent raising the dress in a compromising manner. FIG. 13 illustrates a view 1300 of the limb 400 providing leaning support to the user. As shown, the limb is secured at an angle against a weight of the user leaning backward. Additionally, the foot 460 is opened with the graspers 1010 extending in opposite directions to provide a wider base of support. The foot 460 may be configured with a non-slip coating such as a rubber sole or other similar coating in order to prevent sliding of the limb 400 in the noted configuration.

FIG. 14 illustrates a view 1400 of the limb 400 pivoted around in a similar configuration as shown in the view 1100. That is, the limb extends around the user and provides support to a laptop so that the user can type or otherwise use the laptop with both hands. It should be noted that, the limb 400 can be configured with additional attachments such as trays, different graspers, and so on in order to provide for additional specialized functions. As an additional note, substituting the limb 500 for the limb 400, as previously noted, in various implementations as discussed in relation to FIGS. 6-14 can provide additional dexterity in movement of the limb 500. For example, the limb 500 may extend around the user 605 to provide functionality as shown in views 1100 and 1400 with less intrusion to the user because of the added ability of the limb 500 to curve. Additionally, the limb 500 may provide additional functionality without particular attachments such as curling at a distal end to grasp objects, hold onto railings, open doors, and so on. In either case, the mobility system 170 provides a robust mechanism for assisting users with movements and also with performing daily tasks as shown in the discussed figures.

FIG. 1 will now be discussed in full detail as an example environment within which the system and methods disclosed herein may operate. In some instances, the subsystems 100 are configured to switch selectively between an autonomous mode, one or more semi-autonomous operational modes, and/or a manual mode. Such switching can be implemented in a suitable manner, now known or later developed. "Manual mode" means that all of or a majority of the maneuvering of the limb is performed according to inputs received from a user (e.g., a human operator) whether through mechanical linkages or electronic control inputs. In one or more arrangements, the sub-systems 100 are implemented to operate the limb in only a manual mode.

In one or more embodiments, the sub-systems 100 provide autonomous operation of the limb that is independent of direct user inputs. As used herein, "autonomous" refers to a limb that is automatically operated in an autonomous mode. "Autonomous mode" refers to maneuvering the limb using one or more computing systems with minimal or no input from a human operator. In one or more embodiments, the sub-systems 100 are highly automated or completely automated. In one embodiment, the sub-systems 100 are configured with one or more semi-autonomous operational modes in which one or more computing systems perform a portion of the maneuvering of the limb, and a user provides inputs to perform or initiate a portion of the maneuvering of the sub-systems 100.

The sub-systems 100 can include one or more processors 110. In one or more arrangements, the processor(s) 110 can be a main processor of the sub-systems 100. For instance, the processor(s) 110 can be an electronic control unit (ECU). The sub-systems 100 can include one or more data stores 115 for storing one or more types of data. The data store 115 can include volatile and/or non-volatile memory. Examples of suitable data stores 115 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data store 115 can be a component of the processor(s) 110, or the data store 115 can be operatively connected to the processor(s) 110 for use thereby. The term "operatively connected," as used throughout this description, can include direct or indirect connections, including connections without direct physical contact.

In one or more arrangements, the data stores 115 can store maps including feature-based maps, obstacle maps, or other information that is used by the mobility system 170 and/or the autonomous modules 160 in determining how to control the limb. The one or more data stores 115 can include sensor data 250. In this context, "sensor data" means any information about the sensors that the sub-systems 100 is equipped with, including the capabilities and other information about such sensors. As will be explained below, the sub-systems 100 can include the sensor system 120. The sensor data 250 can relate to one or more sensors of the sensor system 120. As an example, in one or more arrangements, the sensor data 250 can include information on one or more LIDAR sensors 124 of the sensor system 120.

In some instances, at least a portion of the map data and/or the sensor data 250 can be located in one or more data stores 115 located onboard the sub-systems 100. Alternatively, or in addition, at least a portion of the map data and/or the sensor data 250 can be located in one or more data stores 115 that are located remotely from the sub-systems 100.

As noted above, the sub-systems 100 can include the sensor system 120. The sensor system 120 can include one or more sensors. "Sensor" means any device, component and/or system that can detect, and/or sense something. The one or more sensors can be configured to detect, and/or sense in real-time. As used herein, the term "real-time" means a level of processing responsiveness that a user or system senses as sufficiently immediate for a particular process or determination to be made, or that enables the processor to keep up with some external process.

In arrangements in which the sensor system 120 includes a plurality of sensors, the sensors can function independently from each other. Alternatively, two or more of the sensors can function in combination. In such a case, the two or more sensors can form a sensor network. The sensor system 120 and/or the one or more sensors can be operatively connected to the processor(s) 110, the data store(s) 115, and/or another element of the sub-systems 100 (including any of the elements shown in FIG. 1). The sensor system 120 can acquire data of at least a portion of the external environment of the sub-systems 100 (e.g., nearby obstacles).

The sensor system 120 can include any suitable type of sensor. Various examples of different types of sensors will be described herein. However, it will be understood that the embodiments are not limited to the particular sensors described. The sensor system 120 can include one or more limb sensors 121. The limb sensor(s) 121 can detect, determine, and/or sense information about the sub-systems 100 itself including the limb (e.g., limb 400 or 500). In one or more arrangements, the vehicle sensor(s) 121 can be configured to detect, and/or sense position and orientation changes of the limb and/or user, such as, for example, based on inertial acceleration. In one or more arrangements, the limb sensor(s) 121 can include one or more accelerometers, one or more gyroscopes, an inertial measurement unit (IMU), a dead-reckoning system, a global navigation satellite system (GNSS), a global positioning system (GPS), a navigation system, and/or other suitable sensors. The limb sensor(s) 121 can be configured to detect, and/or sense one or more characteristics of the sub-systems 100 and/or the limb itself.

Alternatively, or in addition, the sensor system 120 can include one or more environment sensors 122 configured to acquire, and/or sense data about a surrounding environment. "environment data" includes data or information about the external environment in which the system is located or one or more portions thereof. For example, the one or more environment sensors 122 can be configured to detect, quantify and/or sense obstacles in at least a portion of the external environment of the sub-systems 100 and/or information/data about such obstacles. Such obstacles may be stationary objects and/or dynamic objects. The one or more environment sensors 122 can be configured to detect, measure, quantify and/or sense other things in the external environment of the sub-systems 100, such as, for example, stairs, furniture, railings, doors, curbs, objects, and so on.

Various examples of sensors of the sensor system 120 will be described herein. The example sensors may be part of the one or more environment sensors 122 and/or the one or more limb sensors 121. However, it will be understood that the embodiments are not limited to the particular sensors described.

As an example, in one or more arrangements, the sensor system 120 can include one or more radar sensors 123, one or more LIDAR sensors 124, one or more sonar sensors 125, and/or one or more cameras 126. In one or more arrangements, the one or more cameras 126 can be high dynamic range (HDR) cameras or infrared (IR) cameras.

The sub-systems 100 can include an input system 130. An "input system" includes any device, component, system, element or arrangement or groups thereof that enable information/data to be entered into a machine. The input system 130 can receive an input from a user. The sub-systems 100 can include an output system 135. An "output system" includes any device, component, or arrangement or groups thereof that enable information/data to be presented to the user.

The sub-systems 100 can include one or more limb systems 140. Various examples of the one or more limb systems 140 are shown in FIG. 1. However, the sub-systems 100 can include more, fewer, or different limb systems. It should be appreciated that although particular limb systems are separately defined, each or any of the systems or portions thereof may be otherwise combined or segregated via hardware and/or software within the sub-systems 100. The sub-systems 100 can include a hydraulic system 141, an electrical system 142, and a host system 143. Each of these systems can include one or more devices, components, and/or a combination thereof, now known or later developed.

In one or more arrangements, the hydraulic system 141 includes hydraulic pumps, reservoirs, pressurized lines, actuators, valves, rams, and so on. In general, the hydraulic system 141 can be leveraged to provide movement in the limb and is thus controlled by the mobility system 170 to achieve the noted functions and maneuvers disclosed herein.

In one or more arrangements, the electrical system 142 includes electrical motors, gears, wiring, logic controls, batteries, and so on. In general, the electrical system 142 includes elements designed to control the limb to move in a manner that provides assistance to the user as disclosed herein. Thus, the electrical system 142 is controlled via the mobility system 170 to correlate the actions of the electrical system 142 with desired maneuvers as indicated via the mobility system 170. As an additional note, while both the hydraulic system 141 and the electrical system 142 are disclosed, in various implementations, one of the noted systems may be implemented independently. In further aspects, the systems are implemented in combination.

In one or more arrangements, the limb systems include a host system 143. In general, the host system 143 includes aspects relating to the hose/user of the limb. Thus, the host system 143 can include sensors, support components for securing the disclosed aspects to the user, and so on.

The processor(s) 110, the mobility system 170, and/or the autonomous module(s) 160 can be operatively connected to communicate with the various limb systems 140 and/or individual components thereof. For example, returning to FIG. 1, the processor(s) 110 and/or the autonomous module(s) 160 can be in communication to send and/or receive information from the various limb systems 140 to control the movement, speed, maneuvering, etc. of the limb. The processor(s) 110, the mobility system 170, and/or the autonomous module(s) 160 may control some or all of these limb systems 140 and, thus, may be partially or fully autonomous.

The processor(s) 110, the mobility system 170, and/or the autonomous module(s) 160 can be operatively connected to communicate with the various limb systems 140 and/or individual components thereof. For example, returning to FIG. 1, the processor(s) 110, the mobility system 170, and/or the autonomous module(s) 160 can be in communication to send and/or receive information from the various limb systems 140 to control the movement, speed, maneuvering, heading, direction, etc. of the sub-systems 100. The processor(s) 110, the mobility system 170, and/or the autonomous module(s) 160 may control some or all of these limb systems 140.

The processor(s) 110, the mobility system 170, and/or the autonomous module(s) 160 may be operable to control the navigation and/or maneuvering of the limb by controlling one or more of the limb systems 140 and/or components thereof. For instance, when operating in an autonomous mode, the processor(s) 110, the mobility system 170, and/or the autonomous module(s) 160 can control the direction and/or speed of movements of the limb. The processor(s) 110, the mobility system 170, and/or the autonomous module(s) 160 can cause the sub-systems 100 to move in a particular direction with a designated force, to push against a surface, and so on. In one embodiment, the mobility system 170 can collect data about control signals from the processor 110 and the autonomous module 160 that cause the limb to perform various maneuvers and/or why the autonomous module 160 induced the maneuvers. As used herein, "cause" or "causing" means to make, force, compel, direct, command, instruct, and/or enable an event or action to occur or at least be in a state where such event or action may occur, either in a direct or indirect manner.

The sub-systems 100 can include one or more actuators 150. The actuators 150 can be any element or combination of elements operable to modify, adjust and/or alter one or more of the limb systems 140 or components thereof to responsive to receiving signals or other inputs from the processor(s) 110 and/or the autonomous module(s) 160. Any suitable actuator can be used. For instance, the one or more actuators 150 can include motors, pneumatic actuators, hydraulic pistons, relays, solenoids, and/or piezoelectric actuators, just to name a few possibilities.

The sub-systems 100 can include one or more modules, at least some of which are described herein. The modules can be implemented as computer-readable program code that, when executed by a processor 110, implement one or more of the various processes described herein. One or more of the modules can be a component of the processor(s) 110, or one or more of the modules can be executed on and/or distributed among other processing systems to which the processor(s) 110 is operatively connected. The modules can include instructions (e.g., program logic) executable by one or more processor(s) 110. Alternatively, or in addition, one or more data store 115 may contain such instructions.

In one or more arrangements, one or more of the modules described herein can include artificial or computational intelligence elements, e.g., neural network, fuzzy logic or other machine learning algorithms. Further, in one or more arrangements, one or more of the modules can be distributed among a plurality of the modules described herein. In one or more arrangements, two or more of the modules described herein can be combined into a single module.

The sub-systems 100 can include one or more autonomous modules 160. The autonomous module(s) 160 can be configured to receive data from the sensor system 120 and/or any other type of system capable of capturing information relating to the sub-systems 100 and/or the external environment of the sub-systems 100. In one or more arrangements, the autonomous module(s) 160 can use such data to generate one or more models. The autonomous module(s) 160 can determine position and velocity of the limb. The autonomous module(s) 160 can determine the location of obstacles, or other environmental features.

The autonomous module(s) 160 can be configured to receive, and/or determine location information for obstacles within the external environment of the sub-systems 100/limb for use by the processor(s) 110, and/or one or more of the modules (e.g., 220, 230) described herein to estimate position and orientation of the limb, vehicle position in global coordinates based on signals from a plurality of satellites, or any other data and/or signals that could be used to determine the current state of the sub-systems 100 or determine the position of the sub-systems 100 with respect to its environment for use in either creating a map or determining the position of the sub-systems 100 in respect to map data.

The autonomous module(s) 160 either independently or in combination with the mobility system 170 can be configured to determine travel path(s), current autonomous maneuvers for the limb, future autonomous maneuvers and/or modifications to current autonomous maneuvers based on data acquired by the sensor system 120, and/or data from any other suitable source. In one embodiment, the autonomous module(s) 160 include one or more machine learning algorithms implemented through modules executed by the processor 110. Thus, the in one embodiment, the autonomous module 160 includes the deep learning model 260.

Detailed embodiments are disclosed herein. However, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-14, but the embodiments are not limited to the illustrated structure or application.

The flowcharts and block diagrams in the figures illustrate the architecture, functionality, and operation of possible implementations of systems, methods, and computer program products according to various embodiments. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across several interconnected processing systems. Any kind of processing system or another apparatus adapted for carrying out the methods described herein is suited. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product which comprises all the features enabling the implementation of the methods described herein and, which when loaded in a processing system, is able to carry out these methods.

Furthermore, arrangements described herein may take the form of a computer program product embodied in one or more computer-readable media having computer-readable program code embodied, e.g., stored, thereon. Any combination of one or more computer-readable media may be utilized. The computer-readable medium may be a computer-readable signal medium or a computer-readable storage medium. The phrase "computer-readable storage medium" means a non-transitory storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: a portable computer diskette, a hard disk drive (HDD), a solid-state drive (SSD), a read-only memory (ROM), an erasable programmable read-only memory (EPROM or Flash memory), a portable compact disc read-only memory (CD-ROM), a digital versatile disc (DVD), an optical storage device, a magnetic storage device, or any suitable combination of the foregoing. In the context of this document, a computer-readable storage medium may be any tangible medium that can contain, or store a program for use by or in connection with an instruction execution system, apparatus, or device.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™ Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e. open language). The phrase "at least one of . . . and . . . " as used herein refers to and encompasses any and all possible combinations of one or more of the associated listed items. As an example, the phrase "at least one of A, B, and C" includes A only, B only, C only, or any combination thereof (e.g. AB, AC, BC or ABC).

Aspects herein can be embodied in other forms without departing from the spirit or essential attributes thereof. Accordingly, reference should be made to the following claims, rather than to the foregoing specification, as indicating the scope hereof.

What is claimed is:

1. A mobility system for improving mobility of a user, comprising:
 a support component including at least a waist device that is configured to secure the mobility system to the user at a waist area of the user; and
 a single limb attached to the support component and extendable from the support component to a floor when the user is in a standing position, wherein the single limb is configured to support the user by providing a rigid structure between the floor and the user and in isolation without additional support structures, wherein the single limb is configured to assist the user in transitioning from a seated position to the standing position by applying a substantially upward force to the user through the support component when transitioning to the standing position, wherein the support component is configured to attach the single limb midway on a back of the user aligned with a spine of the user, and wherein the single limb is configured to be wholly aligned with the spine of the user.

2. The mobility system of claim 1, wherein the support component is configured to attach the single limb to the user without attachment to a leg of the user, wherein the limb is formed from tail members arranged in a series, wherein a first one of the tail members is connected with the support component and subsequent ones of the tail members extending away from the support component form a body of the single limb, wherein the tail members are connected together through integrated joints that are configured to provide for the tail members to articulate relative to an adjacent one of the tail members with at least one degree of freedom while securing adjacent ones of the tail members together, and wherein the tail members articulate about a perpendicular axis in a rotational movement.

3. The mobility system of claim 2, wherein the integrated joints include hydraulic members that are selectively controlled to articulate individual ones of the tail members and move the single limb, and wherein each of the tail members is substantially similar in shape, wherein the integrated joints include a joint material that cushions interfaces between the tail members, and wherein each of the tail members include a hollow cavity within a respective central region.

4. The mobility system of claim 1, wherein the limb further includes:

a base joint that is connected with the support component and that is configured to pivot through at least one degree of freedom in order to move the single limb toward and away from the user, a base member connected with a pivoting point of the base joint, wherein the base member is a rigid structure extending from the base joint, a mid-joint that is connected with a distal end of the base member away from the pivoting point of the base joint, wherein the mid-joint is configured to pivot through at least one degree of freedom that includes a same plane of movement as the base joint, a lower member that is a rigid structure connected with the mid-joint and extending from the mid-joint such that the lower member pivots about the mid-joint.

5. The mobility system of claim 4, wherein the base joint and the mid-joint include mechanical ratcheting devices that facilitate extension of the single limb while preventing backlash once motion to the standing position has begun.

6. The mobility system of claim 4, wherein the base joint and the mid-joint include tensioning structures that absorb energy during flexion and release the energy during extension to facilitate upward movement of the user and ratcheting of the mid-joint and the base joint into an extended position that correlates with the standing position of the user, and wherein the tensioning structures include springs that are configured to resist flexion and provide support to the user when transitioning from the standing position to the seated position.

7. The mobility system of claim 4, a foot member connected to a distal end of the lower member that is away from the mid-joint, wherein the foot member contacts the floor and provides an upward force through the single limb.

8. The mobility system of claim 1, wherein the single limb is constructed substantially from at least one of: a metal alloy, or a composite material.

9. The mobility system of claim 1, wherein the single limb is configured to fold into a stowed position on the back of the user.

10. The mobility system of claim 1, wherein the support component further includes a chest device that is configured to attach the system to the user at a chest area of the user, wherein the chest device is connected with the waist device through a spine support that extends between the chest device and the waist device and is substantially rigid, and wherein the waist device includes (i) a belt that is configured to extend around a waist of the user to attach the system to the user and (ii) a seat member that is configured to extend at least partially between legs of the user to provide support to the user through a dispersed area of the seat.

11. The mobility system of claim 1, further comprising:
one or more electronic sensors
one or more processors; and
a memory communicably coupled to the one or more processors and storing:
a monitoring module including instructions that when executed by the one or more processors cause the one or more processors to:
collect environmental sensor data about surroundings of the user and movement sensor data about a present position and trajectory of the user,
analyze the environmental sensor data and the movement sensor data to determine whether an assistance event for actively assisting the user is imminent.

12. The mobility system of claim 11,
a reaction module including instructions that when executed by the one or more processors cause the one or more processors to:
identify an assistance movement for the single limb associated with the assistance event, and
control the single limb to maneuver according to the assistance movement to assist the user and improve mobility of the user.

13. A mobility system for improving mobility of a user, comprising:
a support component including at least a waist device that is configured to secure the mobility system to the user at a waist area of the user; and
a limb attached to the support component and extendable from the support component to a floor when the user is in a standing position, wherein the limb is configured to support the user by providing a rigid structure between the floor and the user,
wherein the limb is configured to assist the user in transitioning from a seated position to the standing position by applying a substantially upward force to the user through the support component when transitioning to the standing position, and
wherein a foot member connected to a distal end of the limb includes a non-slip surface at an interface with the floor, and wherein the foot member includes a claw mechanism that controllably opens and closes to grasp items.

14. A prosthetic device for improving mobility of a user, comprising:
- a support component including at least a waist device that is configured to secure the prosthetic device to the user at a waist area of the user; and
- a single limb attached to the support component and including:
    - a base joint that is connected with the support component and that is configured to pivot through at least one degree of freedom in order to move the single limb toward and away from the user,
    - a base member connected with a pivoting point of the base joint, wherein the base member is a rigid structure extending from the base joint,
    - a mid-joint that is connected with a distal end of the base member away from the pivoting point of the base joint, wherein the mid-joint is configured to pivot through at least one degree of freedom that includes a same plane of movement as the base joint,
    - a lower member that is a rigid structure connected with the mid-joint and extending from the mid-joint such that the lower member pivots about the mid-joint,
- wherein the single limb is configured to support the user by providing a rigid structure between a floor surface and the user and in isolation without additional support structures, wherein the single limb is configured to assist the user in transitioning from a seated position to a standing position by applying a substantially upward force to the user through the support component when transitioning to the standing position,
- wherein the support component is configured to attach the single limb midway on a back of the user aligned with a spine of the user; and
- wherein the single limb is configured to be wholly aligned with the spine of the user.

* * * * *

UNITED STATES PATENT AND TRADEMARK OFFICE
CERTIFICATE OF CORRECTION

PATENT NO. : 10,596,012 B2
APPLICATION NO. : 15/796175
DATED : March 24, 2020
INVENTOR(S) : Jen Strabo Hummelshøj Page 1 of 1

It is certified that error appears in the above-identified patent and that said Letters Patent is hereby corrected as shown below:

In the Specification

Column 15, Line 34: Replace "the hose/user of" with "the host/user of"

Column 17, Line 10: Replace "Thus, the in one embodiment" with "Thus, in one embodiment,"

In the Claims

Column 22, Line 17: Replace "user;" with "user,"

Signed and Sealed this
Eighth Day of September, 2020

Andrei Iancu
*Director of the United States Patent and Trademark Office*